(12) United States Patent
Iliev

(10) Patent No.: US 11,857,369 B1
(45) Date of Patent: Jan. 2, 2024

(54) SYSTEM AND METHOD FOR GENERATION AND DISPLAY OF ULTRASOUND IMAGING DATA

(71) Applicant: Vall A. Iliev, Stow, OH (US)

(72) Inventor: Vall A. Iliev, Stow, OH (US)

( * ) Notice: Subject to any disclaimer, the term of this patent is extended or adjusted under 35 U.S.C. 154(b) by 964 days.

(21) Appl. No.: 16/715,438

(22) Filed: Dec. 16, 2019

Related U.S. Application Data

(63) Continuation-in-part of application No. 13/350,876, filed on Jan. 16, 2012, now abandoned.

(51) Int. Cl.
*A61B 8/00* (2006.01)
*A41C 3/00* (2006.01)
*A61B 8/08* (2006.01)

(52) U.S. Cl.
CPC .......... *A61B 8/4494* (2013.01); *A41C 3/0064* (2013.01); *A61B 8/0825* (2013.01); *A61B 8/4427* (2013.01); *A61B 8/5207* (2013.01); *A61B 8/5215* (2013.01); *A61B 8/565* (2013.01)

(58) Field of Classification Search
None
See application file for complete search history.

(56) References Cited

U.S. PATENT DOCUMENTS

| | | | | |
|---|---|---|---|---|
| 6,102,857 A * | 8/2000 | Kruger | ............ | A61B 5/0507 600/459 |
| 6,358,208 B1 * | 3/2002 | Lang | ............ | A61B 8/4236 600/438 |
| 6,478,739 B1 | 11/2002 | Hong | | |
| 6,749,570 B2 | 6/2004 | Ustuner et al. | | |
| 7,364,592 B2 | 4/2008 | Carr-Brendel et al. | | |
| 7,879,614 B2 | 2/2011 | Krepinsky et al. | | |
| 2006/0173307 A1 | 8/2006 | Amara et al. | | |
| 2007/0123952 A1 | 5/2007 | Strother et al. | | |
| 2008/0281196 A1 | 11/2008 | Somes | | |
| 2009/0259128 A1 | 10/2009 | Stribling | | |
| 2011/0124110 A1 | 5/2011 | Krepinsky et al. | | |
| 2011/0196238 A1 | 8/2011 | Jacobson et al. | | |
| 2011/0237956 A1 * | 9/2011 | Edwards | ............ | A61B 5/0048 600/473 |
| 2011/0306865 A1 * | 12/2011 | Thornton | ............ | A61B 5/0059 600/407 |
| 2013/0225988 A1 * | 8/2013 | Mahfouz | ............ | A61B 5/708 600/430 |

OTHER PUBLICATIONS

Suetens, Paul. Fundamentals of Medical Imaging, 2nd ed. Cambridge, UK, Cambridge University Press. 2009. pp. 2-3. (Year: 2009).*

* cited by examiner

*Primary Examiner* — Joseph M Santos Rodriguez
(74) *Attorney, Agent, or Firm* — GUGLIOTTA & GUGLIOTTA LPA

(57) ABSTRACT

A system and method for remote ultrasonic scanning and informational imaging for neoplasia are provided having a portable ultrasonic transducer integrated with summation software capable of producing a three-dimensional data set. The instant abstract is neither intended to define the invention disclosed in this specification nor intended to limit the scope of the invention in any way.

13 Claims, 7 Drawing Sheets

SYSTEM AND METHOD FOR GENERATION AND DISPLAY OF ULTRASOUND IMAGING DATA

BACKGROUND OF THE INVENTION

1. Field of the Invention

The present invention relates generally to ultrasound imaging, and, more particularly, to a system and method for remote ultrasonic scanning and informational imaging for neoplasia.

2. Description of the Related Art

Each year there are approximately 190,000 women diagnosed with breast cancer and 40,000 women who die of it. Further, according to the National Cancer Institute there are currently more than 2.5 million people who have been affected by breast cancer in their lifetime and according to cancer rates today, 12% of females will be diagnosed with it in their lifetime. This high prevalence rate, combined with the expected survival rate of 98.3% for breast cancer detected while confined to the primary site, reveals how important early detection is to all women, and especially those with increased risk factors. Current screening protocols center on breast self-examinations, even though no study has shown that such examinations reduce breast cancer deaths which may even offer a false sense of security, and on yearly mammograms after the age of forty. Women with increased risk factors are encouraged to start mammograms earlier in their lives, obtain clinical breast exams every three to six months, and consider annual breast Magnetic Resonance Imaging (MRI) screening.

Although mammograms are the golden standards for detecting breast cancer, women have no test of similar or proximate accuracy between mammograms, and for those women with dense breasts, even mammograms sometimes fail to detect a cancer that is present. Dense breasts have more glandular tissue than fat, and fatty tissues produce a black mammogram while dense breasts with more glandular tissue produce white mammograms. Detecting a small potentially cancerous calcification which maps as a white dot in the mammogram may be difficult. Ultrasound, on the other hand, may depict a small potentially cancerous calcification as black, and black may be easier to detect in a background of dense glandular tissue which would be white. Therefore, there is a large population of women in need of a convenient device that can be used in between yearly mammograms to detect changes in the structure of breast tissue to detect tumor growth and simultaneously identify problems that mammograms may have missed in women with dense breasts.

Attempts have been made to implement ultrasound technology as a screening tool between yearly mammograms. However, one of the main problems with current ultrasound diagnostic technologies involves the variability of results depending on the technician performing the diagnostic exam. Different physicians performing the same type of screening test may obtain different results based upon the movement of the ultrasound transducer which decreases the accuracy of using ultrasound as a diagnostic tool.

Another problem with current ultrasound diagnostic technologies involves difficulty with detecting tissue properties such as tissue elasticity, stiffness, morphology, or type. Specifically, tissue elasticity differs between different types of tissue and it is hard for current ultrasound techniques to differentiate between the different types of tissues. This is important because a tumor or other mass will have a different elasticity than surrounding tissues. The ability to distinguish a tumor from surrounding tissues would greatly enhance the possibility of detecting a tumor or other mass at an early stage which may be treatable without adverse consequences.

A search of the prior art did not disclose any patents that read directly on the claims of the instant invention. However, the following references have been found and are considered to be somewhat related.

U.S. Pat. No. 6,478,739, issued in the name of Hong, describes a wearable breast tissue examination device including a support element adapted to fit over at least a portion of a breast of the wearer. The support element has a shell, a measurement apparatus including at least two mutually opposed ultrasound transducer arrays disposed on at least a portion of the inner surface of the shell and at least one bladder element disposed in the shell that is configured to orient the wearer's breast properly for examination. The wearable device may also include means for operatively connecting the two mutually opposed transducer arrays to a transducer driver, and means for holding the support element on the wearer during use.

However, the Hong reference provides an intricate and sophisticated mechanism in order to accurately determine the presence of irregularities in tissue density. In order to accomplish medical level diagnostics, the use of at least two mutually disposed ultrasound transducer arrays arranged on at least a portion of the inner surface of the wearable shell. Further there is a pressurized bladder that is required to provide sufficient contact in order to provide a sonogram quality imaging. Such a device would be expensive to produce, heavy and uncomfortable to wear, and difficult to operate. These, along with other drawbacks, would deter often, regular and widespread usage.

It would be beneficial to provide a tool that may augment the use of home breast exams that are lightweight, simple to operate and inexpensive enough to allow for regular, often and widespread use to obtain an ongoing image profile that can allow for suggested identification of image abnormalities over time. Consequently, to accomplish the same a need exists for providing a novel and effective system and method for remote ultrasonic scanning and informational imaging for neoplasia and the like.

SUMMARY OF THE INVENTION

It is therefore an object of the present invention to provide a system and method for remote ultrasonic scanning and informational imaging for neoplasia.

It is another object of the present invention to provide a system and method for remote ultrasonic scanning and informational imaging for neoplasia or the like directed toward detecting breast cancer.

It is a feature of the present invention to provide a system and method for remote ultrasonic scanning and informational imaging for neoplasia having a portable customizable ultrasonic transducer.

It is another feature of the present invention to provide a system and method for remote ultrasonic scanning and informational imaging for neoplasia having a portable ultrasonic transducer integrated with summation software.

It is yet another feature of the present invention to provide a system and method for remote ultrasonic scanning and informational imaging for neoplasia having a portable ultrasonic transducer integrated with summation software capable of producing a three-dimensional data set that can allow for suggested identification of image abnormalities over time.

Briefly described according to one embodiment of the present invention, a system and method for remote ultrasonic scanning and informational imaging for neoplasia is provided that includes a wearable scanner module that supports a plurality of imaging transducers about the target site in consistent and repeatable geometry. Having sufficient points of reference is critical to monitoring changes in biological function, such as in the progression of a disease state such as neoplasia, and to create this wearable scanner module can be easily and consistently positioned over time about the image target area such as to provide multiple time lapse images that can be transmitted to a user's personal computer, either through portable media or via an extranet or internet network connection. Software compilation of the imaging data obtained through the scanner module allows for identification, and possible characterization, of image abnormalities, such as major blood vessels, which could provide pre-diagnostic information that would allow the user to make a determination if specialized medical diagnostic or treatment is desirable.

By aligning multiple reference points and providing multiple consistent images over time, the present invention may eliminate the main problem with current ultrasound diagnostic technologies, namely, the variability of results depending on the technician performing the exam. Further, an alert may be generated based upon such identified variability of results in order to obtain specialized medical diagnostic or treatment when the pre-diagnostic information of tissue changes occurring over time reaches an alert threshold.

An advantage the System and Method for Generation and Display of Ultrasound Imaging Data of the present invention can provide over other existing technologies includes the use of ultrasound as a medical pre-screening system in which high contrast images can be provided without ionized radiation or radioactive agents and without compression or pain. Further, the use of ultrasound can distinguish between fluid-filled cysts and potentially cancerous tissue at a merely fraction of the cost of a breast MRI or CAT scan.

Further, the present invention provides a simplicity and convenience that can be adapted for at-home use, and can provide graphical imaging output that may enable the individual users to better understand their results, as well as electronically conveying those results to the user's physician who may more quickly determine a proper course of action, if any.

Further objects, features, elements and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

1. Detailed Description of the Figures

Figure 7:
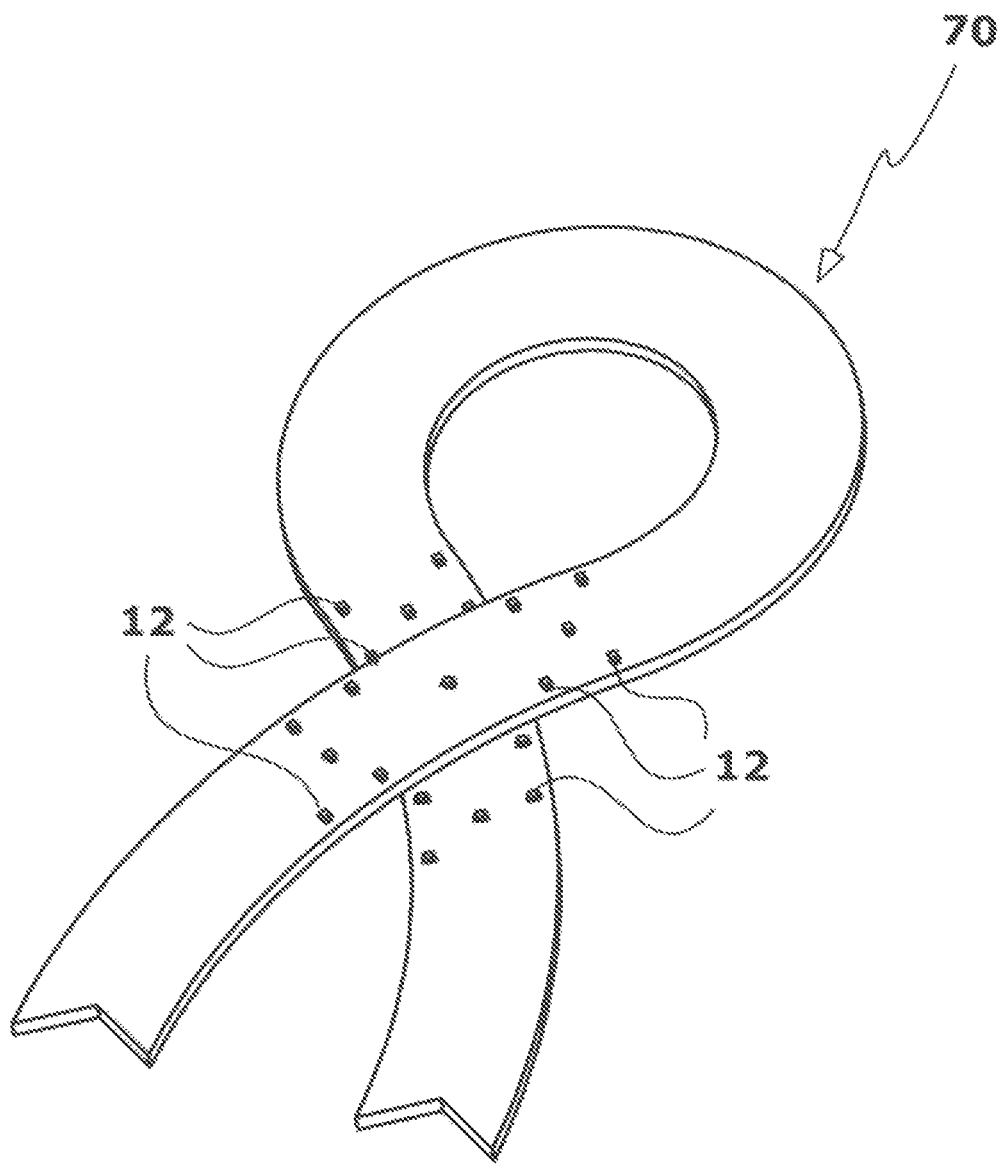
FIG. 7 is perspective view of a perspective view of an alternate exemplary embodiment of a system and method for generation and display of ultrasound imaging data according to the present invention.

Referring to FIG. 1 through FIG. 6, an exemplary embodiment of a system and method for generation and display of ultrasound imaging data according to a preferred embodiment of the present invention is shown incorporating a wearable scanner module, generally noted as 10, for conforming to a target imaging area of a patient. As shown in conjunction with FIG. 1, the wearable scanner module 10 is formed into the shape of a brassiere that can be donned in a closely fitted manner about a user's upper torso. Such a configuration allows for the plurality of imaging transducers 12, to be positioned in a spiral array about a target site of the user's breasts in consistent and repeatable geometry, as well as to provide a minimal size and complexity in order to survey the target site. It should be noted that the use of such a module configuration has been selected as an example of one such design choice that can impart a particular functionality into the current invention. In light of the present teachings, it should subsequently become apparent to a person having ordinary skill in the relevant art that other various module configurations can be equivalently utilized, both for this particular target sight (i.e., scanning of breast tissue), as well as for other utilization with other target sights. By way of example, and not as a limitation, FIG. 7 shows one such proposed alternate configuration of an alternate exemplary embodiment of a system and method for generation and display of ultrasound imaging data according to the present invention in which a scarf shaped module 70 can be donned in a closely fitted manner about a user's upper torso while still allowing for the plurality of imaging transducers 12 to be positioned about a target site of the user's breasts in consistent and repeatable geometry. Similarly, it should be seen that alternate module configurations can further be provided for alternate scan target sites, such as, for example, wearable modules adapted to fit about an elbow, knee, or ankle for use in scanning for soft tissue changes in those particular target areas.

Figure 1:
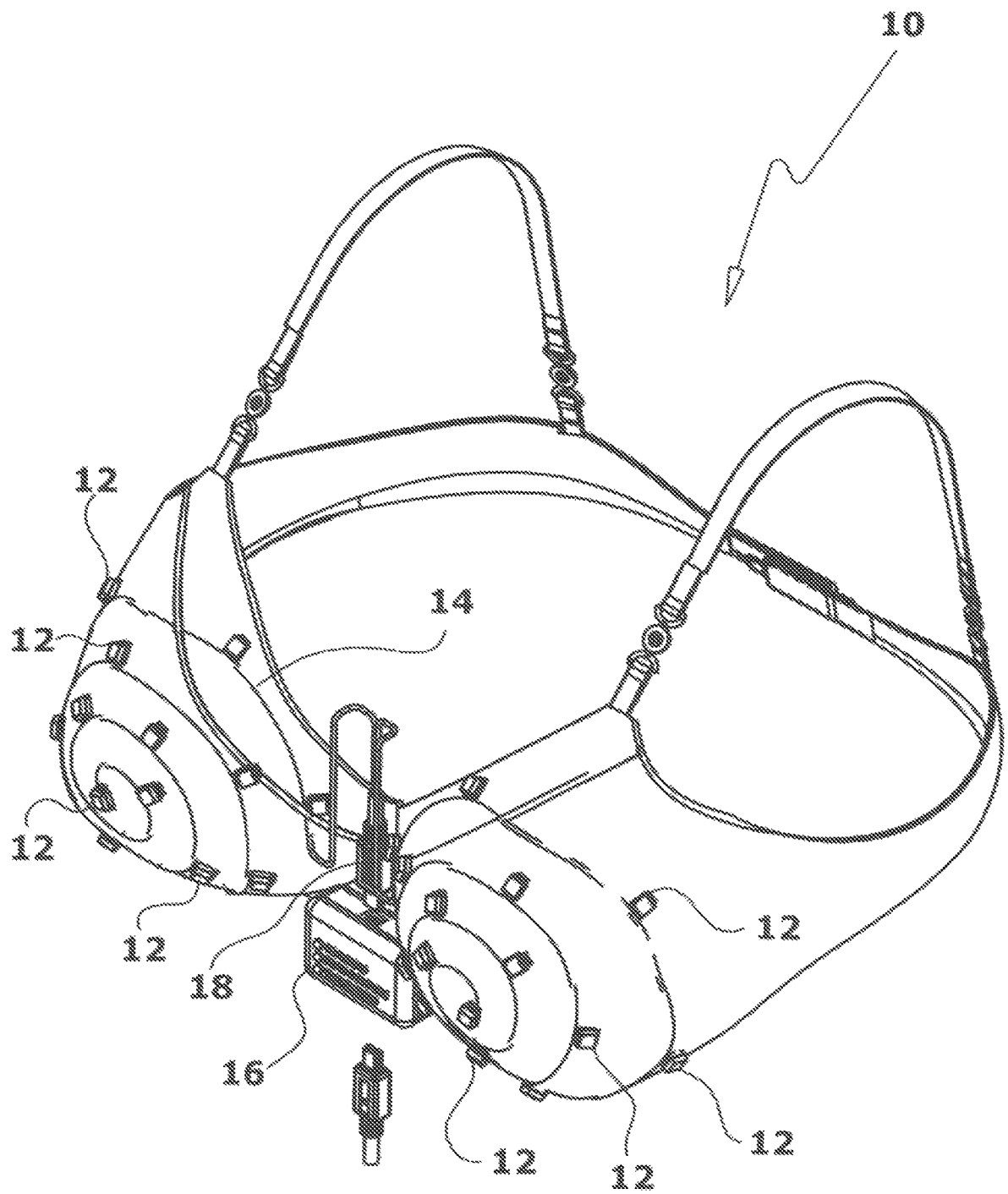
FIG. 1 is a perspective view of an exemplary embodiment of a system and method for generation and display of ultrasound imaging data according to a preferred embodiment of the present invention.
Figure 2:
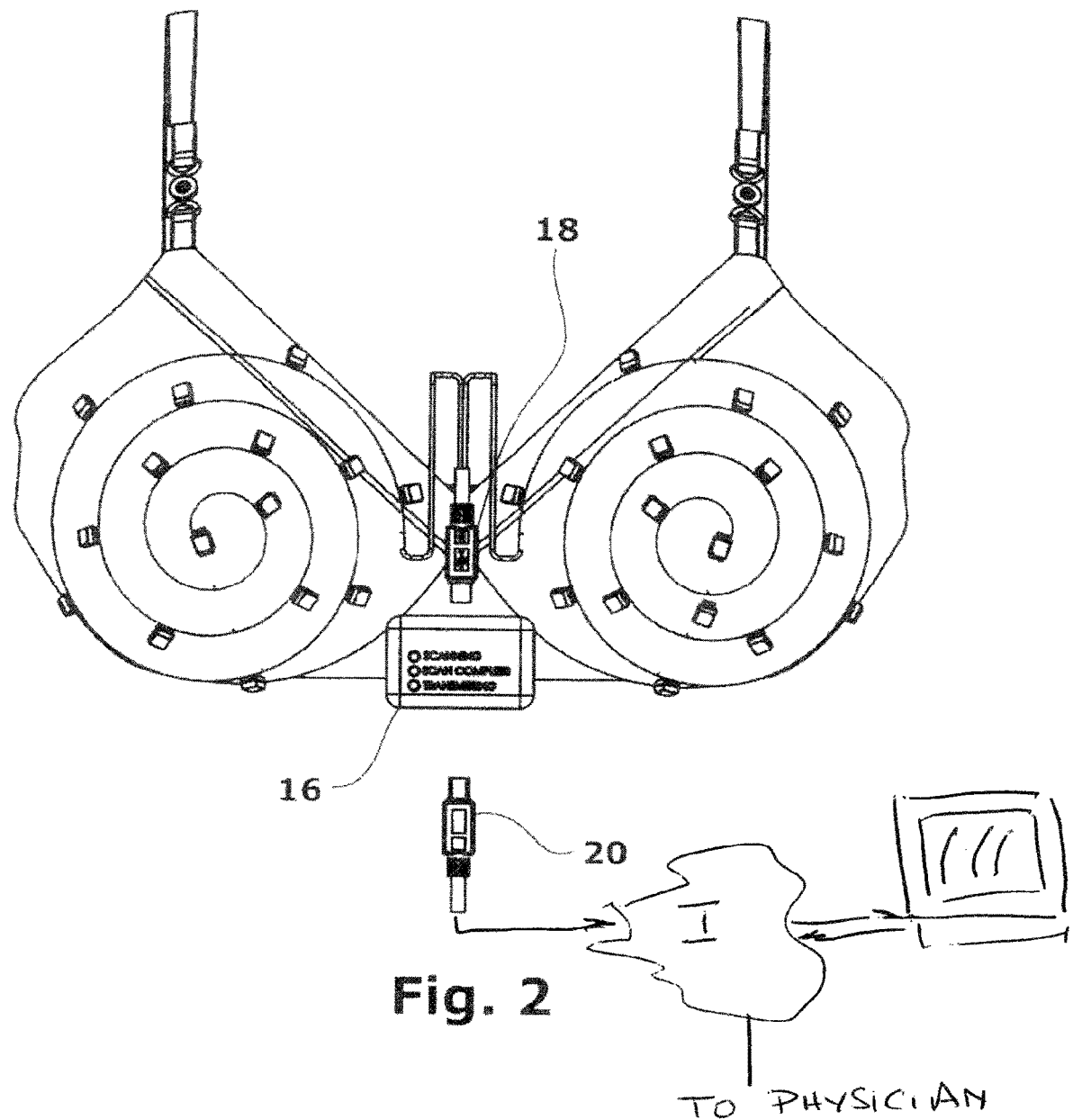
FIG. 2 is a front elevational view thereof.
Figure 3:
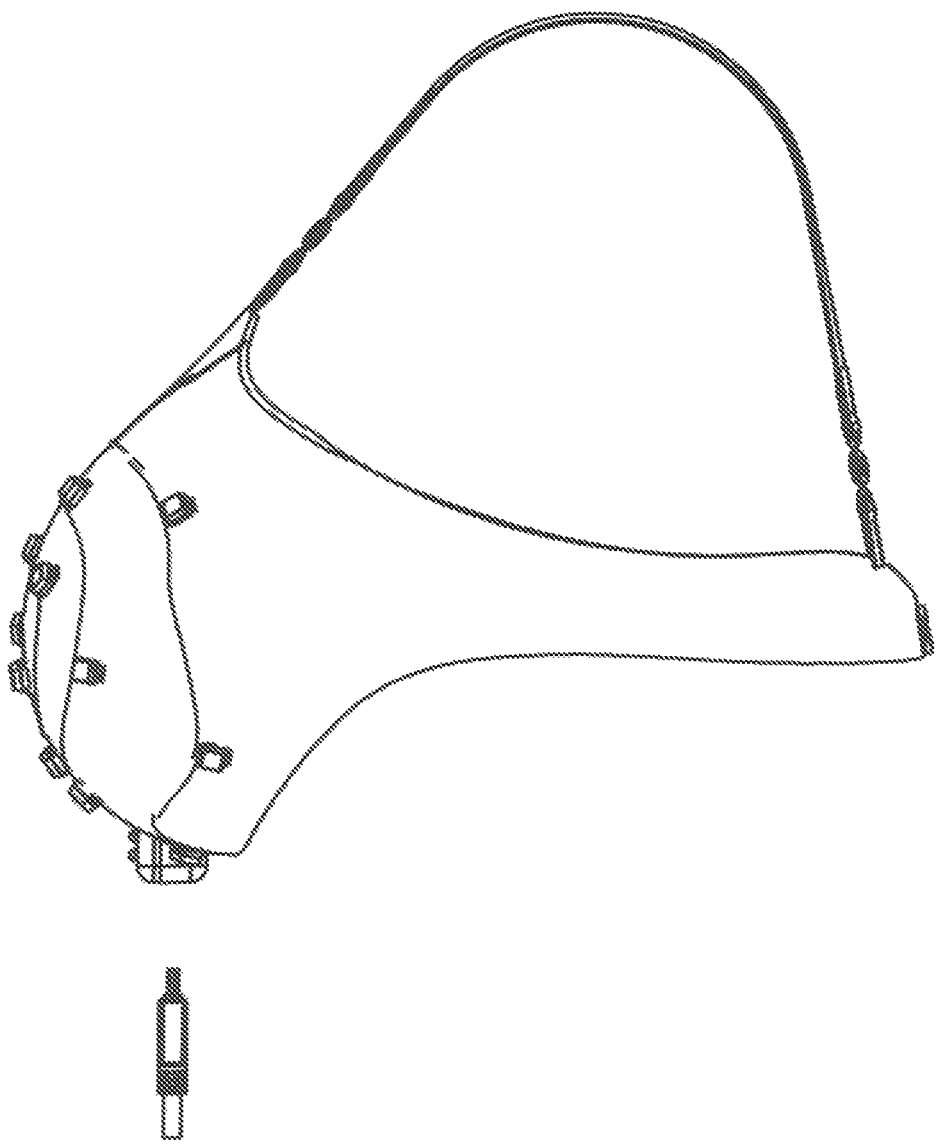
FIG. 3 is a side elevational view thereof.
Figure 4:
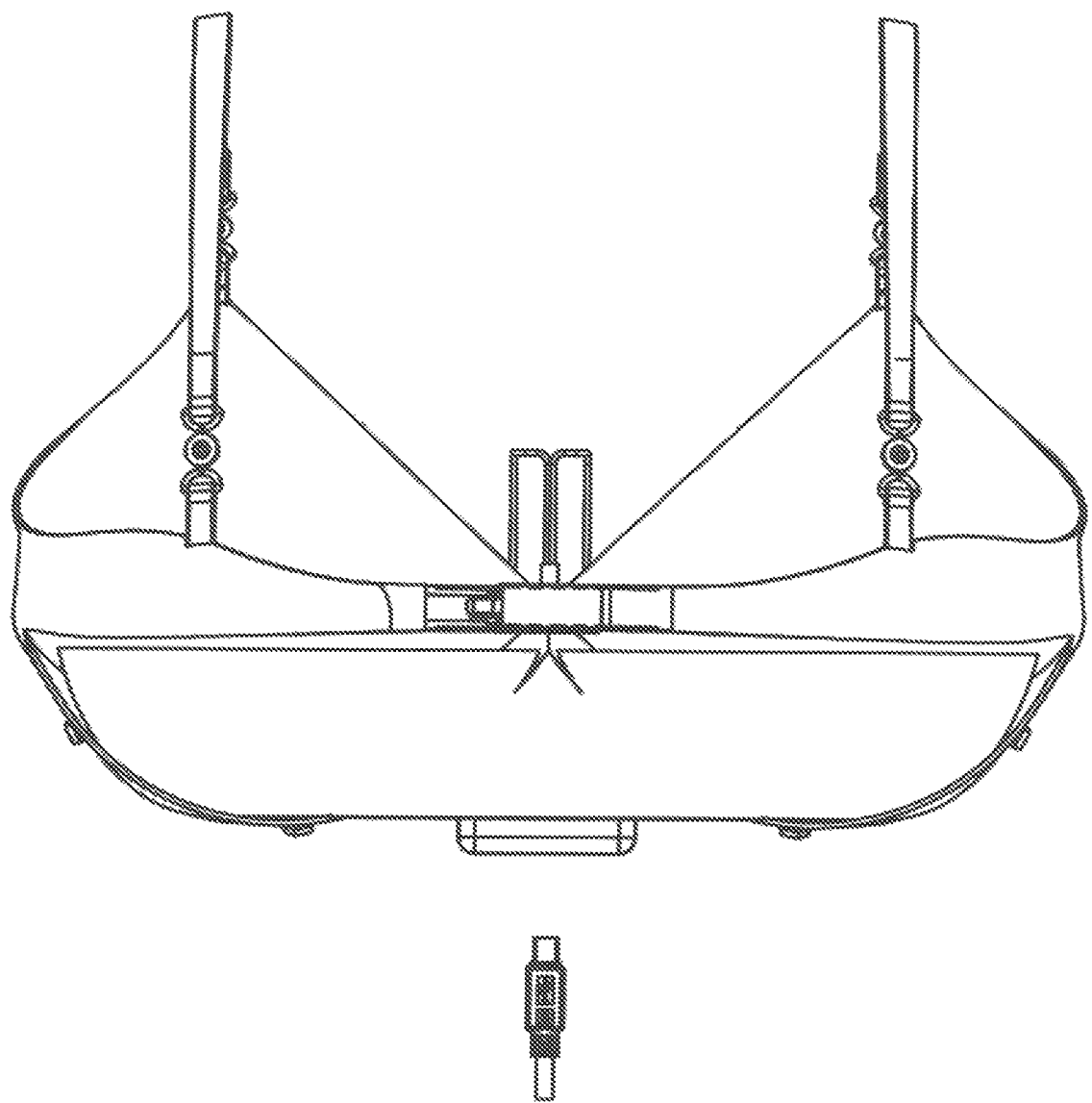
FIG. 4 is a rear elevational view thereof.
Figure 5:
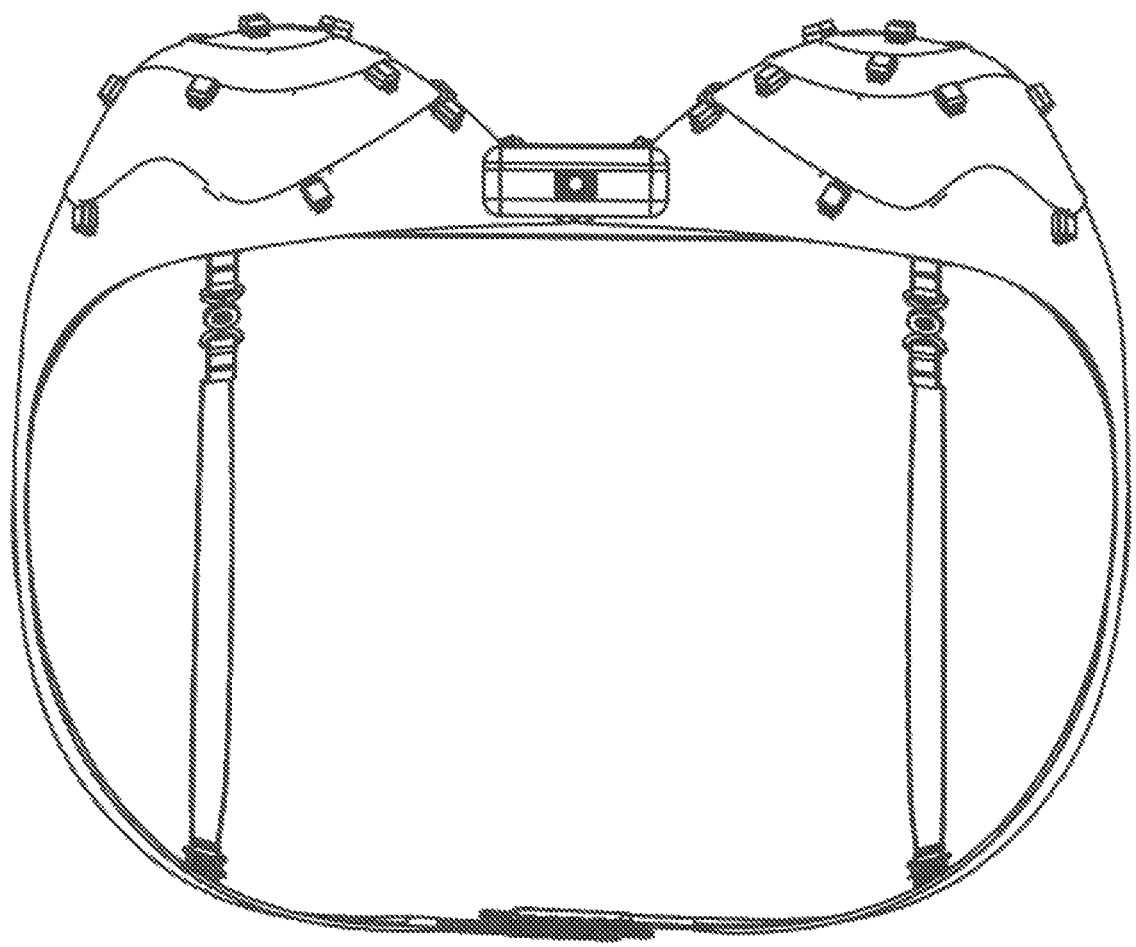
FIG. 5 is a bottom elevational view thereof.
Figure 6:
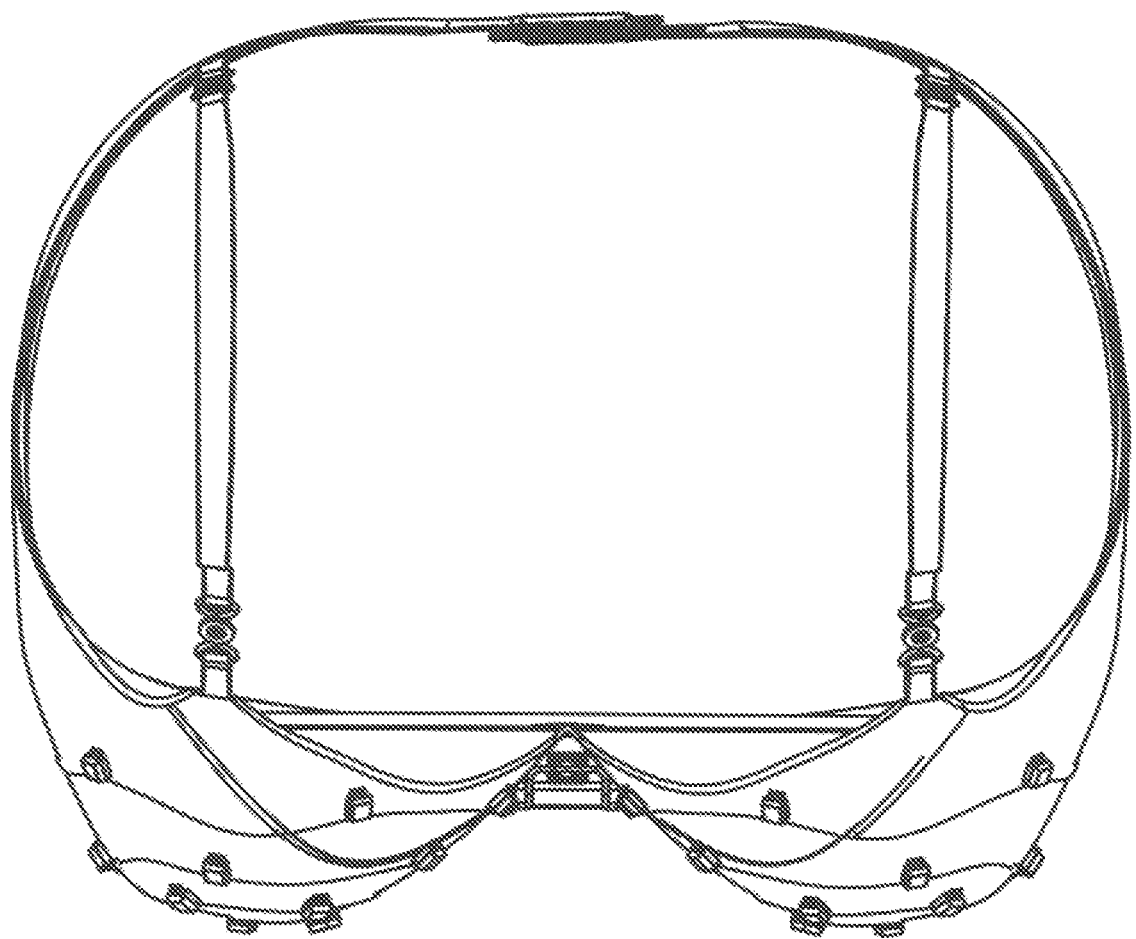
FIG. 6 is a top elevational view thereof.

Utilizing the configurations of FIG. 1 or FIG. 7 for further exemplary enablement, the imaging transducers 12 are positioned such as to have sufficient points of reference is critical to monitoring changes in biological function, such as in the progression of a disease state such as neoplasia. To this end, the wearable scanner module 10, 70 can be easily and consistently positioned over time about the image target area such as to provide multiple time lapse images of sufficient resolution (e.g., corresponding to a frequency of approximately 10 MHz) that can be transmitted to a user's personal computer, either through portable media or via an extranet or internet network connection. The imaging data from the scanner module can further be compiled, transmitted and displayed to a remote physician's computer to allow for suggested identification of image abnormalities.

Software compilation of the imaging data obtained through the scanner module 10 allows for identification, and possible characterization, of image abnormalities. Feature such as changes in major blood vessels or changes in vascularization are features that can be readily imaged using ultrasound, and which also may provide sufficient pre-diagnostic information such as to allow the user to make a determination that anatomical or tissue changes have occurred over time such as to indicate a concern sufficient to obtain specialized medical diagnostic or treatment. Such pre-diagnostic changes may further be compared with healthy levels such that the communication of such data to a physician may be initiated when changes reached a pre-determine threshold. The physician communication may be in the form of an alert generated based upon such identified variability of results in order to obtain specialized medical diagnostic or treatment when the pre-diagnostic information of tissue changes occurring over time reaches an alert threshold.

As shown, the plurality of multiple ultrasonic imaging transducers 12 are aligned in a manner to provide multiple reference points and provide multiple consistent images over time. The array of imaging transducers 12 are in electrical communication with a data bus 14 such as to provide input to an electronics module 16. The electronics module 16 is meant to house a central processing microprocessor sufficient to support obtaining of the data signals, summations of the data into readable images, as well as to register permanent reference features of the body. The electronics module 16 is connectable to the data bus 14 through a data input connection 18. Similarly, a data output connection 20 enables electrical communication with external computer processing resources such as a dedicated computer appliance or a general purpose personal computer. As shown, the electronics module 16 is intended to be small enough to be wearable, yet removable to be portable between scanning functions and reporting functions. As one with ordinary skill in the relevant art should identify, the utilization of such a form factor is not intended to be limiting of the present invention, and the use of other form factors, such as, for example, embedded systems, wireless devices, or other configurations using existing or newly acquired technology is readily imported to the key functionality of the present invention.

2. Operation of the Preferred Embodiment

In operation, the features and benefits of the System and Method for Generation and Display of Ultrasound Imaging Data of the present invention can provide advantages over other existing technologies by including the use of ultrasound as a medical pre-screening system in which the individual user is enabled to obtain, without specialized operational, electrical or medical input or training, with high contrast images. These images are provided without ionized radiation or radioactive agents, and without compression or pain. Such images are referenced automatically to key anatomical features of the particular user, and a plurality of images, obtained over time and referenced to prior images, can be provided in order to provide visual indication of changes to soft tissue related anatomical structures. Such changes may provide an indication of abnormality to a lay user such as to create sufficient curiosity, interest or concern to prompt the user to seek qualified medical review of the situation.

It is further a key operational feature of the present invention to provide a simple and convenient operational package specifically adapted for at-home use. Such a system is intended to provide graphical imaging output that may enable the individual users to better understand their results, as well as electronically conveying those results to the user's physician who may more quickly determine a proper course of action, if any.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of Warner-Jenkinson Company, v. Hilton Davis Chemical, 520 US 17 (1997) or Festo Corp. v. Shoketsu Kinzoku Kogyo Kabushiki Co., 535 U.S. 722 (2002), or other similar caselaw or subsequent precedent should not be made if any future claims are added or amended subsequently to this Patent Application.

Having thus described the invention what is claimed as new and desired to be secured by Letters Patent is as follows:

1. A system for remote ultrasonic scanning and informational imaging comprising a wearable scanner module conforming to a target imaging area of a patient that supports a plurality of ultrasonic imaging transducers about the target site, said scanner module, and plurality of ultrasonic imaging transducers all being affixed to and supported on a wearable structure capable of holding and supporting said scanner module and plurality of ultrasonic imaging transducers in consistent and repeatable geometry, said wearable scanner module comprising:

a brassiere shaped garment having a first support cup and a second support cup, each said support cup connected to an arrangement of attachment straps that can be donned in a closely fitted manner about a user's upper torso;

a first series of ultrasonic imaging transducers in electrical communication with a data bus and supported in a first spiral array on said first support cup, said first series of ultrasonic image transducers adapted to collected scanned data identifying cell and tissue densities within the target imaging area;

a second series of ultrasonic imaging transducers in electrical communication with said data bus and supported in a second spiral array on said second support cup, said second series of ultrasonic image transducers adapted to collected scanned data identifying cell and tissue densities within the target imaging area;

an electronics module removably affixed to said brassiere shaped garment and comprising:
  a central processor;
  an input connection for providing electronic communication between said central processor and said data bus; and
  an output connection adapted for enabling electrical communication between said central processor with an external computer processing resource;

whereas said plurality of ultrasonic imaging transducers are aligned in a manner to provide multiple reference points and provide multiple consistent images over time based on differences in a size or a density from a baseline; and whereas said external computer processing resource is capable of obtaining the data signals, summation of the data into readable images, as well as to register permanent reference features of the body and changes to the reference features of the body over time.

2. The system of claim 1, wherein said electronics module can be alternately affixed to said brassiere shaped garment when in operation and removed from said brassiere shaped garment when not in operation.

3. The system of claim 1, wherein said plurality of ultrasonic imaging transducers are in a spiral arrangement of a number and location such as to provide points of reference to monitoring changes in biological function.

4. A method for facilitating the detection of neoplasia or abnormalities in a breast, comprising:
  a. providing a wearable scanner module of a type of claim 1;
  b. monitoring reference points with said wearable scanner module to indicate changes in biological function;
  c. providing multiple time lapse images with said wearable scanner module;
  d. transferring said multiple time lapse images to a computing resource;
  e. compiling the imaging data obtained through the scanner module on the external computer processing resource for identification of image abnormalities.

5. The method of claim 4, wherein said computing resource comprises a user's personal computer, either through portable media or via an extranet or internet network connection, to provide imaging data adapted to obtain specialized medical diagnosis or treatment.

6. The method of claim 4, wherein said wearable scanner module is adapted for at-home use for providing graphical imaging output to facilitate a compilation of the imaging data obtained through the scanner module for identification of changes in blood vessels or changes in vascularization or tissue changes.

7. The method of claim 4, wherein said graphical imaging output is further electronically conveyed to the user's physician.

8. A method for providing a user with imaging data to provide pre-diagnostic information to make a determination if specialized medical diagnostic or treatment is desirable, said method comprising:
  obtaining multiple imaging data over time through a wearable scanner module conforming to a target imaging area of a patient that supports a plurality of ultrasonic imaging transducers about the target site, said scanner module, and plurality of ultrasonic imaging transducers adapted to identify differences in a size or a density of formations within the target imaging area and all being affixed to and supported on a wearable structure capable of holding and supporting said scanner module and plurality of ultrasonic imaging transducers in consistent and repeatable geometry, said wearable scanner module comprising:
    a brassiere shaped garment having a first support cup and a second support cup, each said support cup connected to an arrangement of attachment straps that can be donned in a closely fitted manner about a user's upper torso;
    a first series of ultrasonic imaging transducers in electrical communication with a data bus and supported on said first support cup;
    a second series of ultrasonic imaging transducers in electrical communication with said data bus and supported on said second support cup;
    an electronics module removably affixed to said brassiere shaped garment and comprising:
      a central processor;
      an input connection for providing electronic communication between said central processor and said data bus; and
      an output connection adapted for enabling electrical communication between said central processor with an external computer processing resource; and
    displaying said imaging data on said computing resource.

9. The method of claim 8, wherein said plurality of ultrasonic imaging transducers are aligned in a manner to provide multiple reference points and provide multiple consistent images over time.

10. The method of claim 9, wherein said central processor is capable of obtaining of the data signals, summation of the data into readable images, as well as to register permanent reference features of the body.

11. The method of claim 9, wherein multiple time lapse images of resolution corresponding to a frequency of between 2.5 MHz to 10 MHz are transmitted to a user's personal computer, either through portable media or via an extranet or internet network connection.

12. The method of claim 11, further comprising compilation of imaging data and comparing image structures over time to identify changes in blood vessels, changes in vascularization or changes in tissue density to create pre-diagnostic information of tissue changes occurring over time.

13. The method of claim 12, further comprising indicating an alert to obtain specialized medical diagnosis or treatment when the pre-diagnostic information of tissue changes occurring over time reaches an alert threshold.

* * * * *